United States Patent [19]

Wojcik et al.

[11] Patent Number: 4,893,956
[45] Date of Patent: Jan. 16, 1990

[54] PACKAGING FOR MEDICAMENTS

[75] Inventors: Michael A. Wojcik; Steven L. Kliff, both of Oak Brook, Ill.

[73] Assignee: Blistex Inc., Oak Brook, Ill.

[21] Appl. No.: 272,916

[22] Filed: Nov. 18, 1988

[51] Int. Cl.$^4$ .................... A45D 33/00; A61M 35/00
[52] U.S. Cl. .................... 401/130; 15/244.2; 15/104.94; 604/289; 206/440; 206/229
[58] Field of Search ............... 401/132, 196, 118, 119, 401/123, 124, 125, 126, 130; 15/104.94, 104.93, 244.2, 209 R, 244.1; 604/289, 310; 427/2; 118/270; 206/229, 438, 440, 363

[56] References Cited

U.S. PATENT DOCUMENTS

| | | | |
|---|---|---|---|
| 2,557,141 | 6/1951 | Rebora | 401/123 |
| 2,810,145 | 10/1957 | Forrow | 401/9 |
| 3,131,410 | 5/1964 | Anderson | 206/229 |
| 3,221,359 | 12/1965 | Moroni | 401/130 |
| 3,299,464 | 1/1967 | O'Brien | 401/132 |
| 3,363,625 | 1/1968 | Jovis | 604/289 |
| 3,386,793 | 6/1968 | Stanton | 401/132 |
| 3,809,483 | 5/1974 | Young | 401/123 |
| 3,860,348 | 1/1975 | Doyle | 401/132 |
| 4,140,409 | 2/1979 | DeVries | 401/132 |
| 4,360,020 | 11/1982 | Hitchcock | 604/289 |
| 4,519,795 | 5/1985 | Hitchcock | 401/132 |
| 4,701,168 | 10/1987 | Gammons | 604/310 |

FOREIGN PATENT DOCUMENTS 983724  2/1965  United Kingdom ............ 15/104.94

*Primary Examiner*—Richard J. Johnson
*Attorney, Agent, or Firm*—Myers & Ehrlich, Ltd.

[57] ABSTRACT

A pad and container assembly wherein the pad comprises a sponge-like center section and a non-permeable protective disk secured to its inner side, which is immersed in a medicament in the bottom of the cup, the disk being pressed against an annular ridge containing the medicament and conforming to its shape to form a seal, the center section of the pad being compressable within the container, the pad having a foldable handle on its upper side which is extendable when the container is opened upon removal of a cover releasably adhered to the outer rim of the container.

13 Claims, 1 Drawing Sheet

PACKAGING FOR MEDICAMENTS

BACKGROUND OF THE INVENTION

This invention relates to a package which incorporates an applicator pad and a cup shaped container.

In previous packages of this type the applicator provided a closure. The applicator or pad was a sponge-like element which fit within the container and absorbed the medication. Fingerhandling of the pad entailed pressing it into the medication in the cup which caused it to ooze through and around the pad between the pad and the surrounding wall of the cup. Greasy medications would deposit on the users fingers and much of it would permeate the pad and was not usable.

DISCUSSION OF THE PRIOR ART

U.S. Pat. No. 3,386,793 discloses a container having liquid polish 26 therein and an applicator pad and cover sealed to the open end of a container.

U.S. Pat. No. 3,860,348 shows a container with a product filled closed tube on the bottom and an applicator sponge fitted into the container and a cover sealing the open end of the container.

U.S. Pat. No. 4,140,409 shows a device with flexible opposed product containers foldable within a sponge.

U.S. Pat. No. 4,360,020 shows a strip of containers with product and sponge in each wherein the pad is saturated with a sterilizing agent and the cover is formed with foldable external tabs to provide a handle.

U.S. Pat. No. 4,519,795 shows a container in which a handle is formed by a pair of tabs folded together and the applicator pad is provided on a cover portion between the tabs.

U.S. Pat. No. 4,701,168 shows a container holding product and a removable cover glued to the open top and various shaped handles on the cover which is secured on its underside to an applicator.

SUMMARY OF THE INVENTION

The primary object of the invention is to provide a novel sterile assembly which comprises a cup-shaped container and a pad closing the container and wherein an impermeable barrier disc is provided on the applicator side of the pad for immersion into a medicament in the bottom of the container, whereby the pad is prevented from absorbing the medicament.

A further object is to form a butterfly handle on top of the pad, which is folded over the top and sealed within a container with the pad.

A further object is to provide a novel hermetically sealed container wherein a sponge like pad is provided with a barrier disc of nonimpressable plastic opposing a topical ointment product deposited in the bottom of the container, the barrier disc being adopted to be dipped into the medication by squeezing the pad into the container and withdrawn for application on the body of the user or onto other surfaces if the product is polish, etc.

A different object is to provide such barrier disk on the inner side of a sponge pad which fits closely to the material of the container in which the sponge is mounted so that as the pad is pressed into the container to dip the disc into the medicament, the barrier disk provides a seal against container body to prevent the medicament, which may have a viscosity similar to that of petroleum, from squirting between the pad and the container body.

Another object is to provide a novel handle for the pad which is made of thin plastic sheet which is glued to the outside of the pad, the sheet being folded at the diameter of the pad to provide a handle folded over a semicircular part of a tab portion.

These and other objects and advantage inherent in and encompassed by the invention will become more apparent from the specification and the drawings, wherein.

DESCRIPTION OF THE INVENTION

Figure 1:
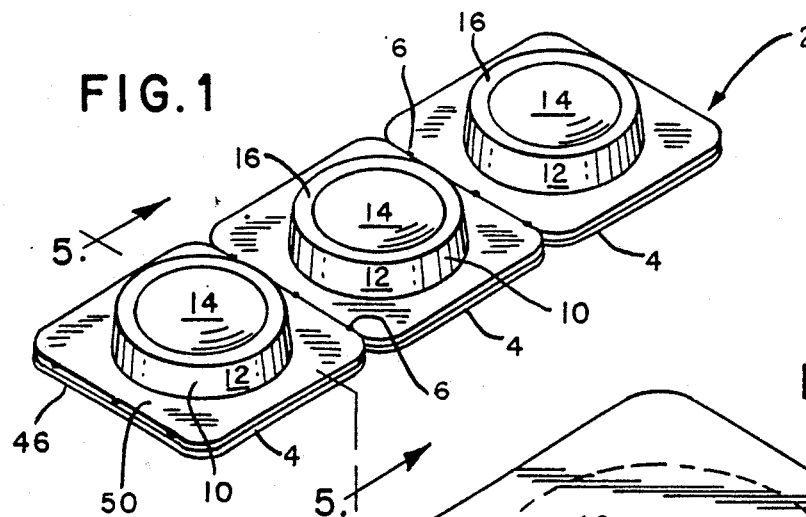
FIG. 1 is a perspective bottom view of a strip of interconnected ointment containers.

The plastic strip generally indicated 2 made of polyethylene or the like comprises connected segments 4. The strip is scored at 6 for easy separation into individual units 8 as in FIG. 2.

Each unit comprises a cup 10 having a frusto-truncated body 12 and an integral bottom 14 with an annular groove 16 circumscribing a depressed center section which contains the ointment 18 or other product of a gel-like consistency such as petroleum gel.

A pad 20 of sponge-like material, such as polyester, is fitted within the body 12 and has a thin barrier disk 22 adhered by any suitable adhesive to the bottom 24 of the disk. The disk, being made of a suitable plastic such as polyethylene, is impermeable and is dipped on its external side 25 into the ointment 18. The disk being a few millimeters in thickness is flexible and when pressed into the cup conforms to the annular ridge 26 at the crest 30 thereof. The disk extends to the perimeter 32 of the pad and has a perimetrical edge 34 which seals against the internal side 36 of the body portion of the cup.

The sponge-like body 38 of the pad fits tightly within the surface 36 of the body of the cup and is compressed therein.

The top side 40 of the pad is glued to the bottom side 42 of the handle structure 44 which has a pair of laterally extending tabs 44' at opposite sides of center fold handle 45 of the plastic material which may also be of polyethylene or the like resin.

Figure 3:
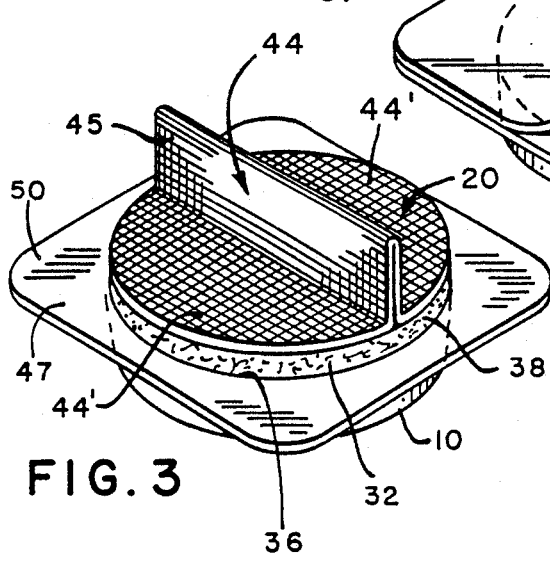
FIG. 3 illustrates an opened container with the handle of the pad extended.
Figure 4:
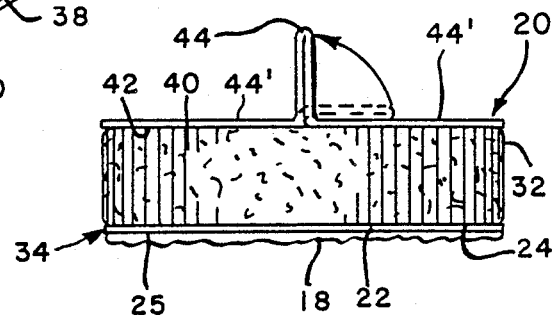
FIG. 4 shows an edge view of the pad with ointment on is bottom.
Figure 5:
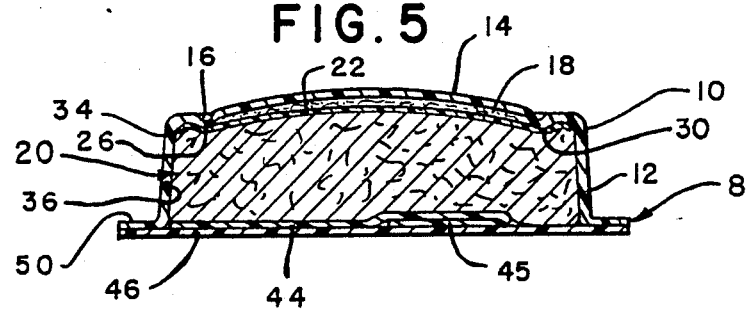
FIG. 5 is an enlarged cross-section taken on line 5—5 of FIG. 1.

The handle portion 45 is shown extended in FIGS. 3 and 4 and folded over in FIG. 5 against one of the securement tabs 44'.

As seen in FIG. 5 the handle portion 45 is depressed into the top of the pad and a cover 46 is laid over the handle and tabs and is glued onto the top surface 47 of an out-turned flange 50 at the top of the cup.

Figure 2:
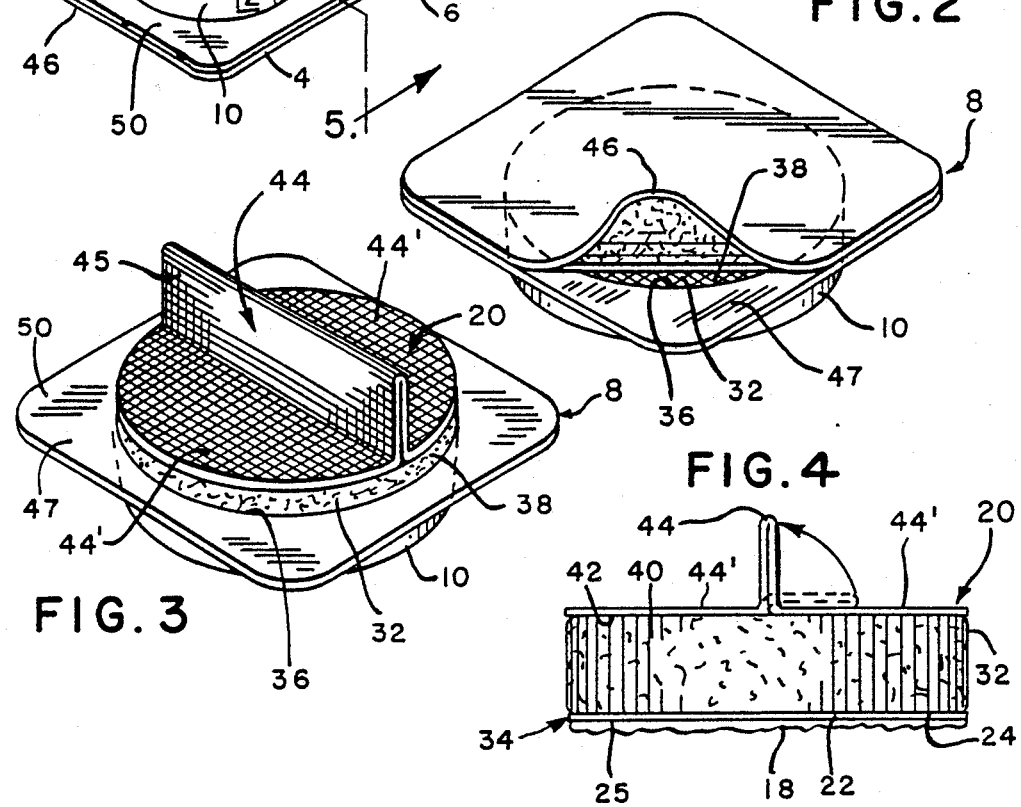
FIG. 2 is a perspective top view of such container showing the cover partially separated from the container preparatory to opening it.

The cover may also be made of polyethylene, polyester, or the like is adapted to be peeled off as seen in FIG. 2 from the releasable adhesive securing the cover to the flange 50.

The handle portion of the pad is raised after the sponge portion expands as seen in FIG. 3.

The applicator is removed from the cup and the emollient or ointment is then rubbed onto the patient.

Inasmuch as the bottom pad cover is non-absorbent the ointment cannot penetrate the sponge body and slides easily on the skin of the user. Furthermore the impermeability of the bottom discs conserves the product so that on the average about three applications can be had. The pad is particularly adaptable for diaper rash. It slides smoothly over the rashes and minimizes injury.

The construction eliminates the messiness usually associated with conventional applicators which absorb the product and ooze out of the pad.

What is claimed is:

1. An applicator comprising a cup-shaped container having a body open at one end and having a bottom at the other end,
   a highly viscous product deposited within said cup, a pad comprising a sponge-like center section having an inner surface,
   a barrier member of non-permeable plastic secured to said inner surface and opposing said product,
   said barrier preventing said product from saturating the pad and providing a smooth surface for engaging the object to which said product is applied.

2. The invention according to claim 1, and
   said barrier having a peripheral edge engageable with the interior of said body to inhibit leakage of the product between said interior surface and said edge.

3. The invention according to claim 2, and
   a handle formed of a thin sheet plastic material foldable into a handle diametrically positioned on the exterior of the pad, said handle being foldable against said pad, and means for closing the open end of the body and pressing said handle to indent said pad.

4. The invention according to claim 1, and
   said bottom having an annular ridge projecting into said container and defining a cavity for containing said product and indenting said barrier member and providing a seal for said product.

5. The invention according to claim 4, and
   said pad in the sealed condition of the container being compressed and pressure-holding said barrier member against said ridge.

6. The invention according to claim 1, and
   said body portion of said container being frusto-conical and said pad wedgingly engaging the same.

7. A sealed applicator package comprising a cup containing an ointment, and
   a pad fitted within said cup and having a nonpermeable disk of plastic secured to the ointment facing side of the pad to prevent saturation of the pad and providing a smooth skin engaging ointment-carrying surface.

8. The invention according to claim 7, and
   said disk and pad having concentric perimeter contacting the interior of the cup, said pad in expanded position being thicker than the depth of the cup and when compressed being equal to the height of the cup and expanding radially into tight engagement with interior surfaces of the cup and holding said disk pressed against a bottom portion of the cup.

9. The invention according to claim 7, and
   said pad having an external side and a butterfly shaped handle structure secured to said external side of the pad and in closed position of the container said handle structure being folded against said external side.

10. The invention according to claim 7, and
    said pad being made of polyurethane foam.

11. The invention according to claim 7, and
    means for holding said pad compressed within the cup and closing the cup.

12. The invention according to claim 7, and
    said cup having an open top, and a releasable plastic cover secured to the top of the cup, and
    a handle secured to the pad and folded against the pad.

13. An ointment-conserving applicator comprising a first disk-like member having an ointment receiving side of nonpermeable material, and
    a second disk-like member of nonpermeable material on the opposite side of the applicator including a foldable handle,
    a compressible sponge-like plastic pad sandwiched between said first and second disk-like members and permanently affixed thereto, said side of said first member on said nonpermeable material preventing the ointment from seeping into said pad.

* * * * *